(12) United States Patent
L'Henoret

(10) Patent No.: US 8,914,217 B2
(45) Date of Patent: Dec. 16, 2014

(54) WAVEGUIDE AND ASSOCIATED AUTOMOTIVE-VEHICLE-BORNE SPECTROMETER

(75) Inventor: Benjamin L'Henoret, Paris (FR)

(73) Assignees: Continental Automotive France, Toulouse (FR); Continental Automotive GmbH, Hannover (DE)

( * ) Notice: Subject to any disclaimer, the term of this patent is extended or adjusted under 35 U.S.C. 154(b) by 755 days.

(21) Appl. No.: 13/141,224

(22) PCT Filed: Dec. 15, 2009

(86) PCT No.: PCT/EP2009/008998
§ 371 (c)(1),
(2), (4) Date: Aug. 23, 2011

(87) PCT Pub. No.: WO2010/072362
PCT Pub. Date: Jul. 1, 2010

(65) Prior Publication Data
US 2011/0295484 A1 Dec. 1, 2011

(30) Foreign Application Priority Data
Dec. 23, 2008 (FR) ..................................... 08 07381

(51) Int. Cl.
*F02D 45/00* (2006.01)
*G01N 21/27* (2006.01)
(Continued)

(52) U.S. Cl.
CPC ............ *G01N 21/05* (2013.01); *G01N 2201/08* (2013.01); *F02D 2200/0611* (2013.01);
(Continued)

(58) Field of Classification Search
CPC ....... F02D 41/1451; G01J 3/02; G01J 3/0256; G01J 3/42; G01N 21/31; G01N 21/359; G01N 21/534; G01N 33/2888

USPC .................... 356/70, 417; 250/301, 343, 225; 701/102; 73/23.37, 23.4
See application file for complete search history.

(56) References Cited

U.S. PATENT DOCUMENTS 3,696,247 A * 10/1972 McIntosh et al. ......... 250/339.07
4,329,048 A * 5/1982 Capitini et al. .................. 356/73
(Continued)

FOREIGN PATENT DOCUMENTS

JP          04 032748 A    2/1992
WO        03/030621 A2    4/2004

OTHER PUBLICATIONS

International Search Report, dated Jan. 28, 2010, from corresponding PCT application.

*Primary Examiner* — Hai Huynh
*Assistant Examiner* — Gonzalo Laguarda
(74) *Attorney, Agent, or Firm* — Young & Thompson

(57) ABSTRACT

A device for measuring a spectrum of a light beam in a wavelength range chosen beforehand, device called a spectrometer, the spectrum being generated by a fluid to be analyzed, the spectrometer including:
  at least one light source;
  a measurement cell including the fluid to be analyzed;
  a measurement detector placed on an optical pathway taken by a measurement optical beam being emitted by the light source and encountering the measurement cell; and
  a reference detector placed on an optical pathway taken by a reference optical beam being emitted by the light source and not encountering the measurement cell,
wherein the spectrometer is borne by an automotive vehicle and includes an element for forming an incident optical beam emitted by the at least one light source, and for dividing the optical beam into a measurement beam and a reference beam, in the form of a waveguide.

15 Claims, 4 Drawing Sheets

Figure 1:
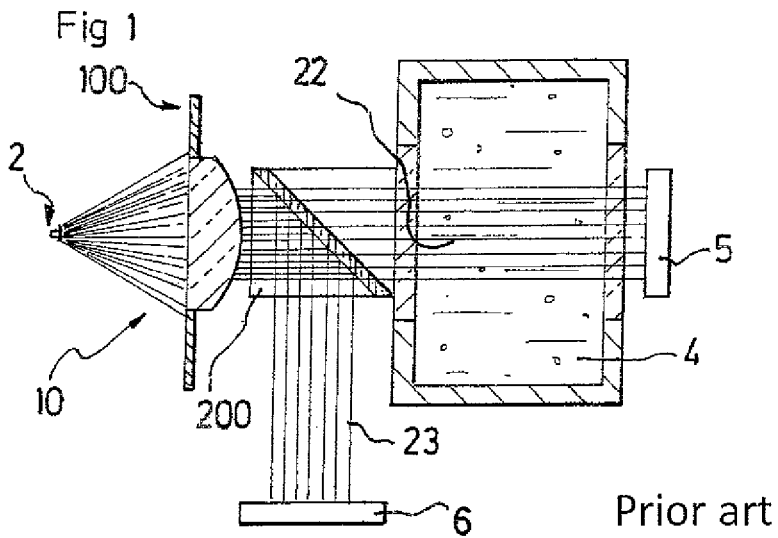

(51) Int. Cl.
*G01N 21/31* (2006.01)
*F02D 19/06* (2006.01)
*G01N 21/05* (2006.01)
*G01N 21/35* (2014.01)
*F02D 41/00* (2006.01)

(52) U.S. Cl.
CPC ............ *G01N 21/359* (2013.01); *G01N 21/274* (2013.01); *F02D 41/0025* (2013.01); *G01N 21/31* (2013.01); *F02D 19/0634* (2013.01); *G01N 2021/317* (2013.01); *G01N 2201/0627* (2013.01)
USPC ........................................................ 701/102

(56) References Cited

U.S. PATENT DOCUMENTS

| | | | | |
|---|---|---|---|---|
| 5,049,742 | A | * | 9/1991 | Hosonuma et al. ............ 250/301 |
| 5,166,755 | A | * | 11/1992 | Gat ................................ 356/419 |
| 5,739,916 | A | * | 4/1998 | Englehaupt .................... 356/414 |
| 6,043,505 | A | * | 3/2000 | Ames et al. .................... 250/577 |
| 7,339,657 | B2 | * | 3/2008 | Coates ............................ 356/73 |
| 7,715,008 | B2 | * | 5/2010 | Hamby et al. ................. 356/417 |
| 8,525,444 | B2 | * | 9/2013 | Van Duijneveldt ........... 315/308 |
| 8,768,600 | B2 | * | 7/2014 | Blanc et al. .................... 701/102 |
| 2002/0069021 | A1 | * | 6/2002 | Takezawa et al. .............. 702/28 |
| 2011/0313635 | A1 | * | 12/2011 | Blanc et al. .................... 701/102 |

* cited by examiner

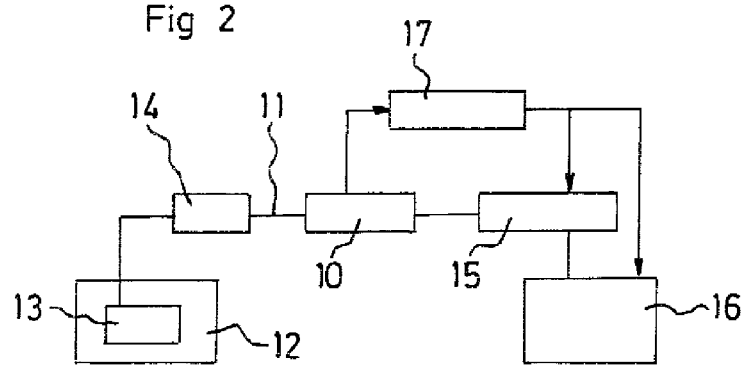
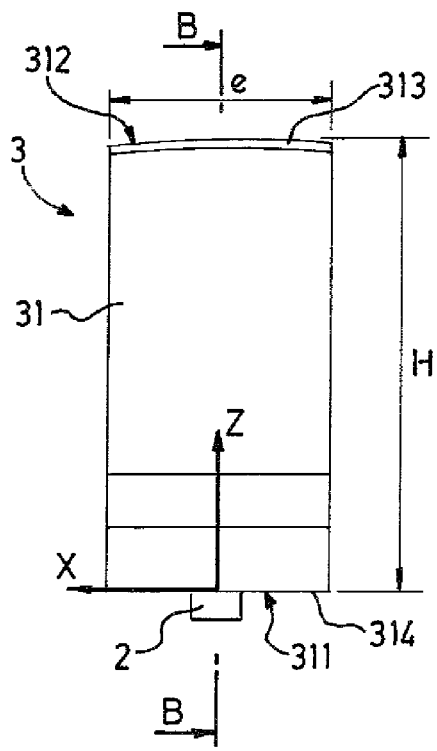
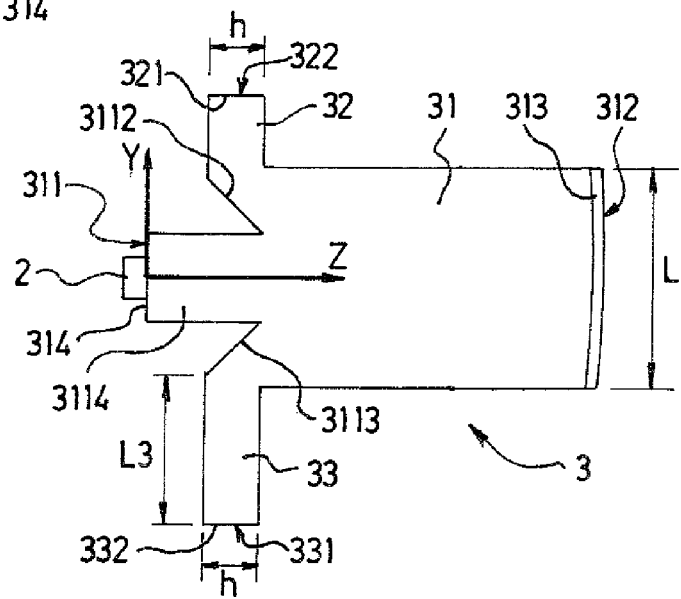

WAVEGUIDE AND ASSOCIATED AUTOMOTIVE-VEHICLE-BORNE SPECTROMETER

The present invention relates to the field of automotive-vehicle-borne electronics. More particularly it relates to optoelectronic instruments. More specifically, it relates to spectrometry suitable for determining the composition of a fluid.

Competition between the various automobile manufacturers leads to an unceasingly renewed pursuit of better operational performance, in terms of both fuel consumption and ecological characteristics. In the field of vehicles driven by internal combustion engines, the composition of the fuel has a direct impact on the performance of the engine. Consequently, knowing the precise composition of the fuel allows certain of the operating parameters of the engine to be adjusted to improve combustion and render the vehicle less polluting.

Moreover, this knowledge may also allow detection of mistakes (filling a petrol tank with diesel and vice versa) that could possibly damage the engine, and allow the driver to be alerted or even to allow ignition to be blocked (for a controlled internal combustion engine) so as to prevent irreparable damage. It is also possible to detect a fuel that does not meet legal quality standards.

Similar observations apply to the engine oil, even to the coolant or to other fluids the properties of which influence the operation of the vehicle.

One means of achieving this compositional analysis of a fluid is to use spectrometric technology.

It is recalled that a spectrometer is a measurement instrument intended to determine the absorption of certain wavelengths of the spectrum (generally of light) by a sample to be analyzed. The wavelengths absorbed form peaks in the absorption spectrum and characterize certain molecules or components present in said sample.

As defined in the context of the present invention, an optical spectrometer is therefore mainly composed of a light source, an optical assembly for forming the light beam so as to create a parallel beam able to pass through the sample, a wavelength filter allowing measurement in a certain wavelength range, and a light detector which measures the light intensity received at this wavelength.

Spectrometers working in the ultraviolet (UV), visible and near infrared (IR) wavelength ranges are already in day-to-day use in many fields.

All these fields of application use the same type of measurement instrument, only the size and portability characteristics of which vary. Such instruments optionally use various technologies (Fourier transform, filter, monochromator, diffraction system, etc.) and do not operate over a wide temperature range. This is because, for reasons related to drift in their performance depending on the temperature, they are rarely used in environments that experience large temperature variations. This is the main obstacle to their use in the automotive field which requires vehicle-borne hardware to be effective between −40° C. and +105° C.

In an application such as that considered in the field of measuring automobile fluids, it is moreover necessary to use very low unit cost components that are robust in time, so as to guarantee a reliable and lasting operation. One solution is to use light emitting diodes (LEDs) as the light source.

In fact, light emitting diodes are very reliable, well-known components that have a very low cost because they are used in very high volumes in a multitude of applications. They are moreover at the present time available in many wavelength versions, allowing their use in a spectral range from 300 nm (near ultraviolet) to 2500 nm (near infrared).

Nevertheless, the emission spectrum and optical power properties of the light emitting diodes varies substantially depending on the current flowing through them and the ambient temperature in which they are used. Interpretation of the measured absorption requires the intensity at a given wavelength, of the light wave sent through the sample to be analyzed, to be known precisely.

Their use as a light source for spectroscopy, in environments the temperature of which may vary significantly (for example from −40° C. to +105° C. in an automobile) therefore requires innovative solutions in order to compensate for the natural variation in their properties. More generally, these observations relate to all light sources whose performance varies with aging and temperature.

Low-cost spectrometer devices using an LED-based technology are already known, capable of taking into account drift in the light source.

For example, a spectrometer 10 comprises, as illustrated in FIG. 1:
- at least one light source 2;
- means 100 for shaping at least one incident optical beam output by the at least one light source 2;
- a measurement cell 4;
- a measurement detector 5 placed on an optical pathway of a measurement optical beam 22, said measurement optical beam 22 encountering the measurement cell 4, and
- self-calibration means allowing any drift of the light source 2, due to environmental conditions or conditions of use, to be taken into account independently of whether a fluid to be analyzed is present in or absent from the measurement cell 4, said self-calibration means comprising:
  - means 200 for creating a reference optical beam 23, said reference optical beam being output by the light source 2, and not encountering the measurement cell 4; and
  - a reference detector 6 placed on an optical pathway of the reference optical beam 23.

The forming means 100 are for example a system of lenses or mirrors.

The optical power of a lens is characterized by the shape of its surfaces, by its dimensions, by the material from which it is made and by the refractive index difference between the material from which the lens is made and the medium in which the lens is immersed (Snell's law). Generally, the lenses are employed in air, a medium having a refractive index close to 1.

The optical power of a mirror is characterized, for its part, essentially by the shape of its surface.

During a significant drop in temperature, as frequently occurs in the automotive field, moisture present in the air condenses on the surfaces of the optical components of the spectrometer, thereby causing non-negligible interference. On the one hand, the deposition of fine droplets on the surfaces of the optical components causes their optical powers to be modified (water is a medium having a refractive index of 1.33), thus compromising the formation of the light rays and thereby degrading the characteristics of the spectrometer. On the other hand, the spectrometer being intended, among other quantities monitored, to measure the amount of water in a fluid (in a fuel for example), introducing water droplets onto the measurement optical pathway causes an error to be introduced into the measurement of the amount of water in the fluid.

The use of optical components within the spectrometer in environments the temperature of which may vary significantly therefore requires innovative solutions in order to obviate the effects of condensation or dirt.

A first solution consists in placing the optical components under vacuum or in an inert gas. This solution requires a container ensuring confinement of an atmosphere or maintenance of a vacuum so as to ensure a sealed environment. This solution is however unsuitable (mainly in terms of the manufacturing costs) to use in automobile environments.

Another solution consists in embedding the optical components in a resin transparent at the wavelengths used by the spectrometer, for example a silicone or epoxy resin. However, the refractive index of the materials used for this embedding depends on the pressure and stresses created during the polymerization of the resin and this solution leads to variations that are not easily controlled, thereby compromising the shaping of the rays.

Known solutions are therefore unsuitable for use of this technology in the context of automobile-borne applications such as the measurement of the chemical composition of a fuel or of its properties.

The aim of the invention is therefore to provide a spectrometer design meeting size, reliability and performance constraints compatible with automobile applications.

A second aim of the invention is to make low-cost production possible making its use feasible.

A third aim of the invention is to provide a vehicle-borne spectrometer that may be used for a number of applications to different fluids, without hardware modification.

For this purpose, one subject of the invention is a device for measuring a spectrum of a light beam, in a wavelength range chosen beforehand (this type of measurement device commonly being called a spectrometer), said spectrum being generated by a fluid to be analyzed.

The spectrometer comprises:
at least one light source;
a measurement cell, comprising the fluid to be analyzed;
a measurement detector placed on an optical pathway taken by a measurement optical beam, said measurement beam being emitted by the light source, and encountering the measurement cell; and
a reference detector placed on an optical pathway taken by a reference optical beam, said reference beam being emitted by the light source and not encountering the measurement cell.

According to the invention, the spectrometer is borne by an automotive vehicle and furthermore comprises a means for shaping an incident optical beam (emitted by the at least one light source) and for dividing said optical beam into a measurement beam and a reference beam. The forming means being a waveguide.

The waveguide comprises:
a first volume for forming and separating the incident beam emitted by the light source, said light source being pressed against a first end of the first volume;
a second volume for guiding the measurement beam towards the measurement detector, said second volume being pressed, via a free end, against a first wall of the measurement cell;
a third volume for guiding the reference beam towards the measurement detector, said third volume being pressed, via a free end, against the reference detector.

The first volume comprises, at an end, called a second end, opposite the first end, a face, called a reflective face, treated at least on a part of its surface so as to reflect the incident beam emitted by the light source.

The first volume furthermore comprises, substantially at the first end and on either side of the light source, a face treated so as to direct the measurement beam and the reference beam, respectively, into the second volume and the third volume, respectively, of the waveguide.

The waveguide comprises a fourth volume for holding the measurement detector, said measurement detector being pressed, by means of said fourth volume, against the first wall of the measurement cell.

Preferably, the untreated faces of the waveguide absorb or scatter wavelengths emitted by the light source.

Advantageously, the waveguide is made of a plastics material that allows the spectrum emitted by the light source to pass. In one embodiment, the waveguide is made of polymethylmethacrylate (PMMA) or of polycarbonate (PC).

In one embodiment, the waveguide is produced using an injection molding method.

Alternatively to the plastics material, the waveguide is made of glass and allows the spectrum emitted by the light source to pass.

Preferably, the spectrum emitted by the fluid to be analyzed is an absorption spectrum.

In another embodiment, the spectrum emitted by the fluid to be analyzed is an emission spectrum.

Preferably, the measurement detector and reference detector are each associated with a wavelength filter.

In a preferred embodiment, the light source is formed by four light emitting diodes (LEDs) the emission spectrum of which covers a wavelength range corresponding to the fluid to be analyzed, said light emitting diodes being arranged in a square and as close to one another as possible.

Alternatively, the light source is an incandescent lamp.

The invention also relates to a sensor of fuel, oil, coolant or urea quality intended to be installed permanently in a vehicle, comprising a spectrometer as described.

The invention also relates to a method for controlling at least one operating parameter of a vehicle engine, said vehicle being provided with a sensor as described, and an electronic control unit connected to said sensor. The method comprises steps of:
selecting the fluid to be analyzed;
turning on the light source at regular intervals;
waiting for a suitable period of time taking account of the normal initialization time of said light source;
controlling the variable filters so as to set said filters in succession to the various wavelengths forming a series necessary for determining the composition of the fluid analyzed, these wavelengths being stored beforehand in a memory of said control unit for each fluid likely to be analyzed by the sensor;
measuring, for each wavelength selected, using the measurement detector and the reference detector, the light intensity received at this wavelength;
transmitting to the control unit, at regular intervals, measurements of the absorption spectrum of the fluid to be analyzed and measurements of the reference spectrum;
comparing, using the control unit, the measurement value and the reference value;
determining, using the control unit, the absorption due to the sample contained in the measurement cell;
determining, based on an algorithm or a data table stored in memory, using the control unit, at regular intervals, modifications to the operating parameters of the engine.

The invention also relates to a vehicle employing a device as described, or a method as described.

Figure 3:
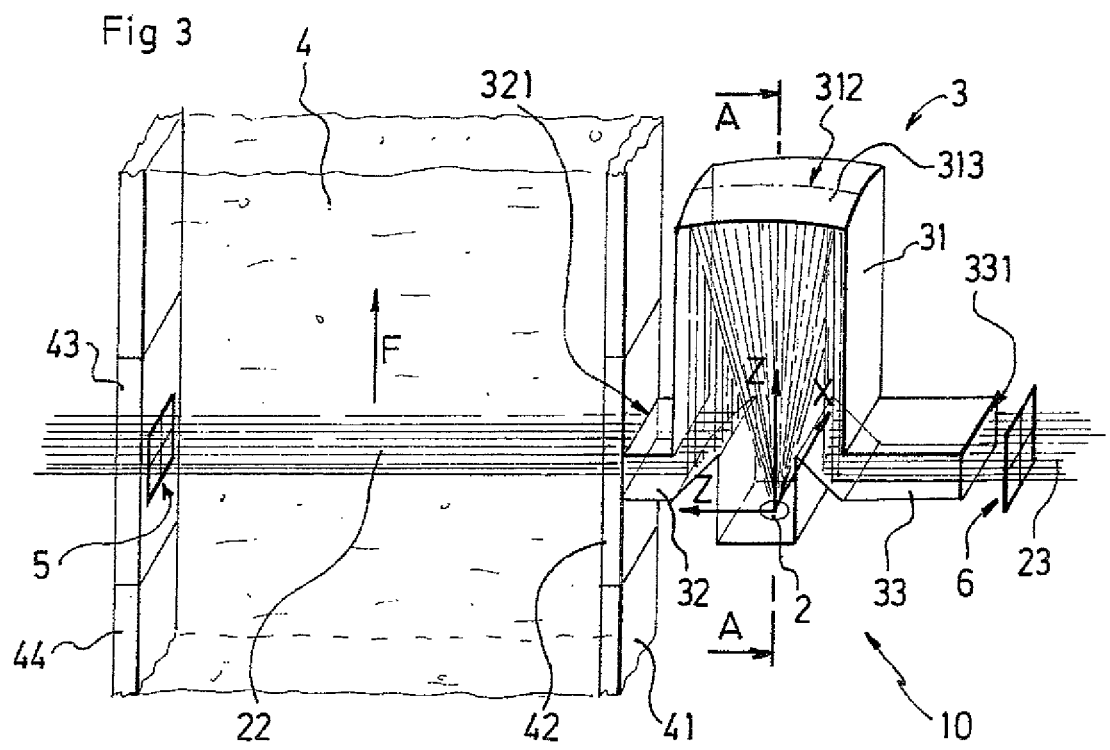
Figure 6:
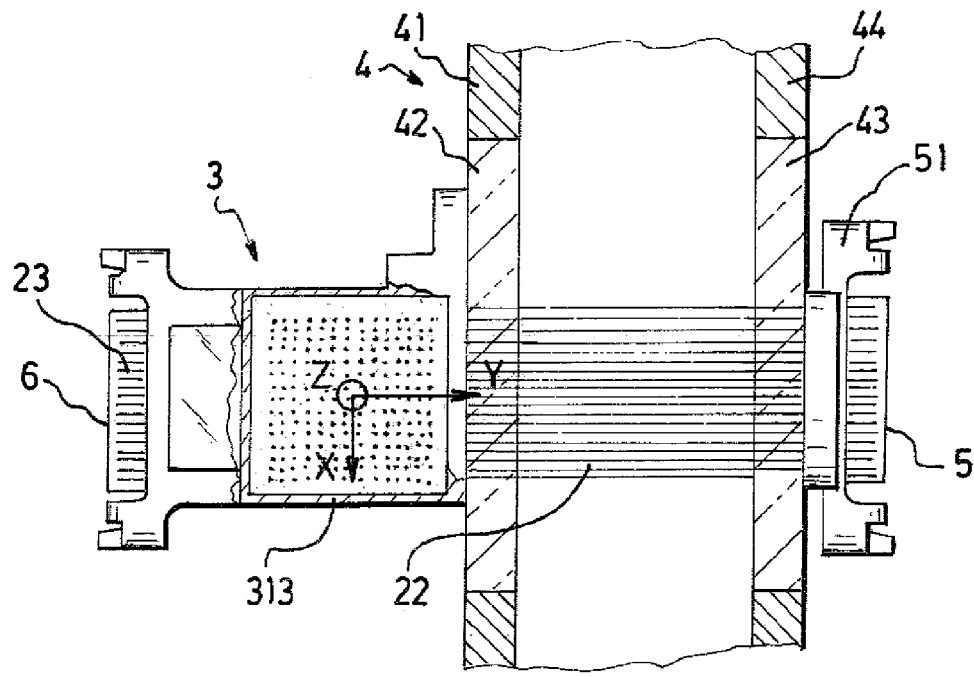
Figure 7:
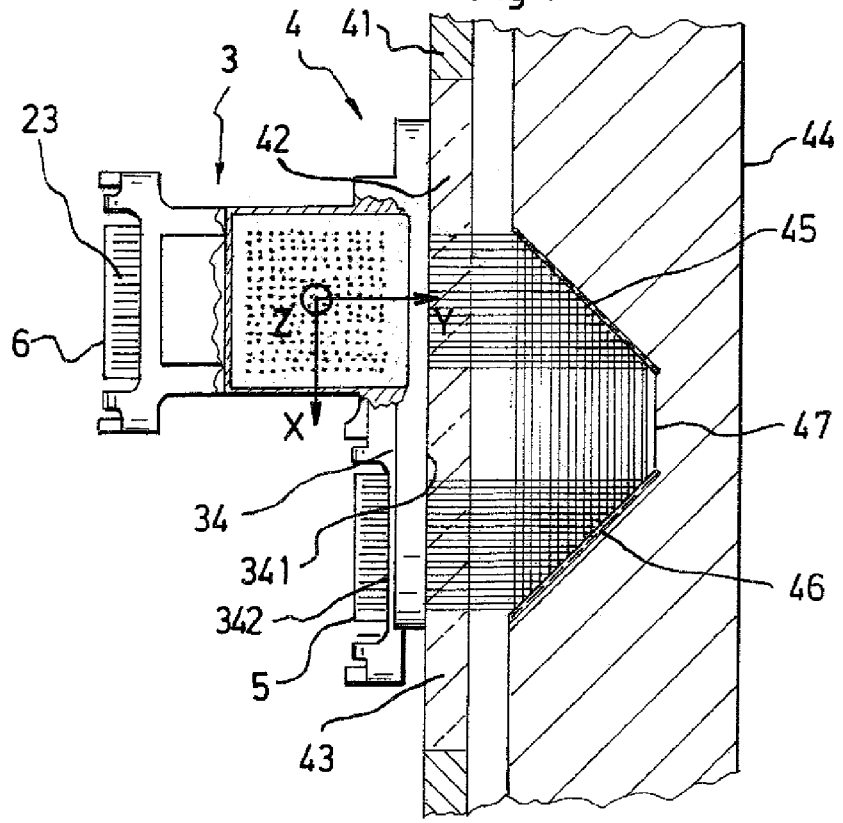
Figure 8:
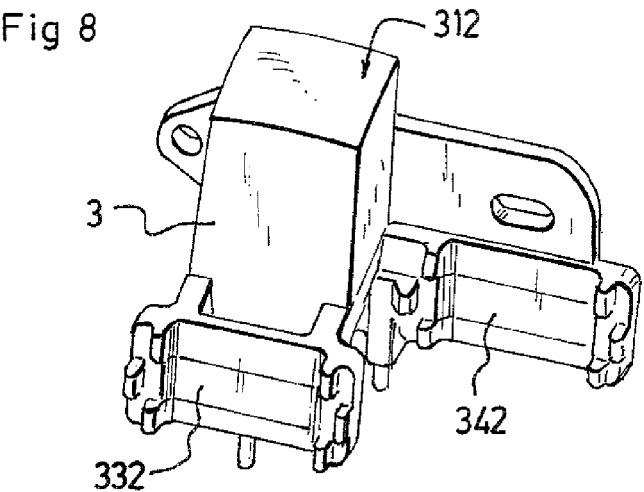
Figure 9A:
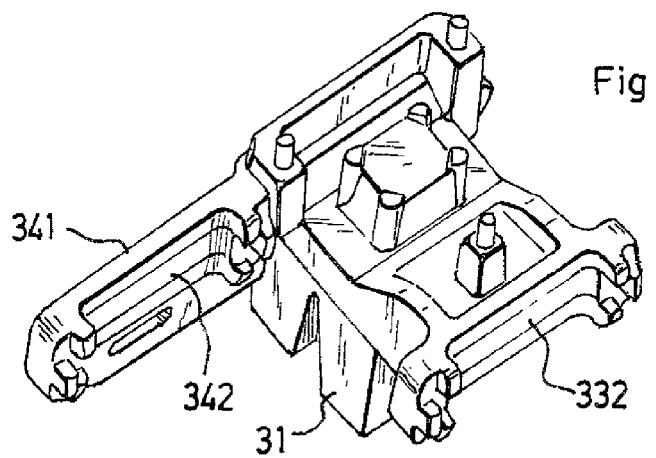
Figure 9B:
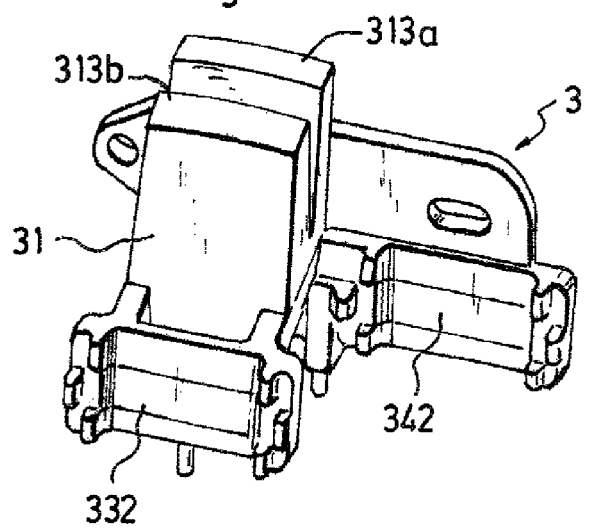

The detailed description of the invention is given with reference to the figures showing:
in FIG. 1, already mentioned, a spectrometer according to the prior art;

in FIG. 2, an exemplary integration of a spectrometer according to the invention into a fuel circuit of an automotive vehicle;

in FIG. 3, a perspective view of a spectrometer in a first embodiment of the invention;

in FIG. 4, a schematic of the waveguide of FIG. 3 in cross section along the line AA;

in FIG. 5, a schematic of the waveguide of FIG. 4 in cross section along the line BB;

in FIG. 6, a functional schematic top view of a spectrometer for a difficult environment according to one embodiment of the invention;

in FIG. 7, a schematic functional top view of a spectrometer for a difficult environment according to a second embodiment of the invention;

in FIG. 8, a perspective view of the waveguide according to the second embodiment of the invention; and in FIGS. 9a and 9b, various perspective views of a variant of the waveguide according to the second embodiment of the invention.

The exemplary embodiment of a device, for measuring a spectrum of a light beam, according to the invention, called a spectrometer 10, is described in the case of an application, to a fuel circuit of an automotive vehicle, for measuring the quality of the fuel. However, the invention is also applicable to other circuits of an automotive vehicle, for example for measuring oil, coolant or urea. More generally, the invention is applicable to the measurement of the quality of fluids in difficult (temperature, physical access) environments.

As illustrated in FIG. 2, the spectrometer 10 according to the invention is advantageously placed on a fuel pipe 11, downstream of the tank 12 and of a fuel pump 13, also downstream of the fuel filter 14 (so as to reduce measurement errors), but upstream of an injection pump 15 and of an internal combustion engine 16.

The spectrometer 10 is connected to an electronic control unit 17, which is also connected to the injection pump 15 or to the engine 16 certain settings of which it is able to control. It is noted that this electronic control unit 17 can be either the engine control unit, conventionally present in automotive vehicles, or a control unit of the spectrometer, which sends the values of the parameters of the fluid analyzed directly to the engine control unit.

The spectrometer 10 according to the invention, described relative to FIG. 3, is structured about a measurement cell 4 in which the fluid to be analyzed, which is fuel in this exemplary application, flows (arrow F).

The spectrometer 10 comprises:
a light source 2;
a waveguide 3, for guiding an incident optical beam emitted by the light source 2;
the measurement cell 4, containing the fluid to be analyzed;
a measurement detector 5, placed on an optical pathway taken by a measurement optical beam 22, said measurement beam 22 being emitted by the light source 2 and encountering the measurement cell 4; and
a reference detector 6, placed on an optical pathway taken by a reference optical beam 23, said reference beam 23 being emitted by the light source 2 and not encountering the measurement cell 4.

In the following description, an orthogonal coordinate system XYZ is defined centered on the light source 2. Z defines a longitudinal axis corresponding to the flow direction of the fluid in the measurement cell 4, Y defines a transverse axis normal to walls 41, 44 of the measurement cell 4 and X defines an axis orthogonal to the two other axes.

The light source 2, the emission spectrum of which corresponds to the wavelength range corresponding to the fluid to be analyzed, comprises at least one light emitting diode.

In the present nonlimiting case, the light source 2 is formed by four light emitting diodes arranged in a square as close to one another as possible, on the same holder, in the XY plane, so as to minimize measurement shifts related to the distance between the four light emitting diodes. The light source 2 emits in the positive-Z direction. The emission peaks of the light emitting diodes are located about 810 nm, 875 nm, 935 nm and 1020 nm, respectively.

For example, the light source has an area of 0.3×0.3 mm, with a distance of 0.1 mm between two contiguous light emitting diodes.

The waveguide 3 has a dual purpose. On the one hand, the waveguide 3 forms the incident optical beam emitted by the light source 2. On the other hand, it divides the incident beam into two beams, so as to create a first beam, the reference beam 23, which is directed towards the reference detector 6, and a second beam, the measurement beam 22, which is directed towards the measurement detector 5.

Preferably, the waveguide 3 is made of a plastics material, such as polymethylmethacrylate (PMMA) or polycarbonate (PC). It may, in a variant, be made out of glass molded using known techniques.

Advantageously, the waveguide 3 is produced using an injection molding technique, allowing complex parts to be produced at a reasonable cost.

The waveguide 3 consists of a single unit split up into three volumes so as to allow the incident beam to be returned either towards the reference detector 6, or towards the measurement detector 5:
a first longitudinal volume 31, mainly extending along the positive-Z direction;
a second transverse volume 32, mainly extending along the positive-Y direction;
a third volume 33, also transverse, mainly extending along the negative-Y direction.

The first volume 31 of the waveguide 3 is larger in size and allows the incident beam to be formed. The expression "to be formed" is understood to mean that the incident beam is collimated and separated into two substantially parallel and identical beams.

The first volume 31 is symmetric in the XZ and YZ planes and has a thickness e, along the X-axis, a height H, along the Z-axis, and a length L, along the Y-axis, as illustrated in FIGS. 4 and 5.

In this exemplary application, the height H is equal to 30 mm, the length L is equal to 15 mm and the thickness e is equal to 15 mm.

The second volume 32 and the third volume 33, respectively, have a thickness identical to that of the first volume and a height h sufficient for the measurement beam 22 and the reference beam 23, respectively, to pass—about 2 mm.

The length $L_3$ of the third volume 33 is adjustable depending on the location desired for the reference detector 23. In this example, $L_3$ lies between 5 and 15 mm.

The light source 2 is advantageously pressed against, preferably bonded onto, an external face 314 of a first end 311 of the first volume 31, and emits in the positive-Z direction.

The reference detector 6 is advantageously pressed against, preferably bonded onto, an external face 332 of a free end 331 of the third volume 33.

The pressing (or the bonding) of the optical components against (onto) the waveguide advantageously allows the problem of condensation possibly appearing on the surfaces of the optical components, during a large temperature variation in the external environment of the spectrometer 10, to be obviated.

The first volume 31 comprises at a second end 312, opposite the first end 311, a spherical, concave face 313 of radius R in the YZ plane and of radius R' in the XZ plane.

The face 313 is treated so as to reflect the beam incident from the light source 2. In the rest of the description, the face 313 is called the internal reflective face.

The radii R and R' of the reflective face 313 are chosen depending on the height H, the length L and the thickness e so that the beams reflected by said face 313 are parallel to the Z-axis.

In an exemplary embodiment of the invention, the radius R is equal to 61.65 mm and the radius R' is equal to 61.65 mm (the surface of the reflective face 313 is a section of a sphere in the present example). The radius is located on the Z-axis, just above the center of the light source (just above the center of the four diodes in the embodiment illustrated).

By way of example, the length L of the first volume 31 is 30 mm for a radius R of the spherical surface of 61.65 mm.

Thus, the incident, uncollimated beam emitted by the light source 2 is directed towards the reflective face 313 which collimates the beam and separates it into two separate reflected beams, the reference beam 23 and the measurement beam 22, both parallel to the Z-axis and in the negative-Z direction.

The first volume 31 comprises, substantially at the first end 311 and on either side of the light source 2, a face 3112, 3113 treated so as to reflect the beam 22, 23 reflected by the internal face 313. The faces 3112, 3113 are for example covered with a layer of a substance reflective to the wavelengths of said light source. The two faces 3112, 3113 are oriented at 90° to each other. A first face 3113 allows the reference beam 23 to be directed into the third volume 33, the other face 3112 allows the measurement beam 22 to be directed into the second volume 32.

It should be noted here that the faces 3113 and 3112 may also function using total reflection between the plastics material and the air (45° angle of incidence). The problem is then that this total reflection may be disrupted by condensation. This is why in the preferred embodiment these faces are covered with a reflective substance (gold for example).

The two faces 3112, 3113 are formed of surfaces that are planar over the entire thickness of the waveguide 3 and oriented, for the first face, at 45° in the YZ plane, and for the second face, at 135° in this same plane. They are separated by a cavity 3114 that allows the incident beam to pass into the first volume 31 of the waveguide 3.

The faces 3112 and 3113, respectively, have dimensions so as to return all of the measurement beam 22 and the reference beam 23, respectively, towards the measurement detector 5 and the reference detector 6, respectively.

The reflective character of the faces 313, 3112 and 3113 is obtained by polishing and metallization of said three faces (for example with chromium), using means known to a person skilled in the art.

Preferably, so as to prevent the propagation of stray rays (propagation by multiple reflections from nonoptical faces of the part 3), the internal faces of the waveguide 3 which are not polished and/or metallized are optically absorbent (or scattering) at the wavelengths of the light source 2, for example by applying a layer of black paint thereto. The external faces of the waveguide 3 which are not polished and/or metallized are optically opaque to the light beams located in the external environment. This arrangement is not however required if the spectrometer 10 is placed in an opaque (for example black) box which does not allow external light to propagate towards the waveguide.

The waveguide 3 is pressed, preferably bonded, via the free end 321 of the external face 322 of the second volume 32 to a first window 42 in the wall 41 of the measurement cell 4.

The measurement detector 5 is pressed, preferably bonded, to a second window 43 in the wall 44 of the measurement cell 4.

In a first embodiment of the spectrometer, illustrated in FIGS. 3 and 6, the measurement detector 5 is independent of the waveguide 3.

The measurement cell 4 is here formed by a segment of a tube, of rectangular cross section, equipped with two parallel windows 42, 43, facing each other on two opposite walls 41, 44 of the measurement cell 4.

The two windows 42, 43 may be for example made of glass or plastics material, this material must be chemically neutral with respect to the fluid analyzed, undeformable as a function of temperature, and transparent in the wavelength range used for the measurement (here the near infrared, but wavelength ranges in the UV/visible may also be used without modification to the spectrometer described).

The measurement cell 4 is made of metal or of a rigid plastics material, so that the distance between the two windows remains substantially unchanged as a function of temperature, the aim being to prevent interference with the measurement. The windows 42, 43 are fixed to the walls 41, 44 of the measurement cell 4 by bonding or any other known means.

The measurement cell 4 is connected at its two open ends (not shown), by means known to a person skilled in the art, to a tube 11 for circulating fuel, previously installed in the vehicle.

To measure the absorption spectrum, the measurement beam 22, when output from the waveguide 3, therefore passes through the first window 42, through a thickness of fluid to be analyzed equal to the width of the measurement cell 4 along the transverse axis Y and then through the second window 43 of the measurement cell 4. During this transit, certain wavelengths of the emission spectrum of the light source 2 are attenuated due to absorption of photons at these wavelengths by molecules present in the fluid.

The attenuated measurement beam 22, emitted by the measurement cell 4 along the transverse axis Y, is sensed by the measurement detector 5, placed on the optical pathway of the measurement beam 22, and pressed against, preferably bonded to, the second window 43, for example by means of a holder 51 made of a material that is preferably identical to that of the waveguide 3.

The reference beam 23, when output from the third volume 33 of the waveguide 3, is sensed by the reference sensor 6.

In an exemplary embodiment, the measurement detector 5 and/or the reference detector 6 is a pyroelectric detector associated with a variable filter, such as for example a Fabry-Perot interferometric cavity. The Fabry-Perot cavity is a MEMS (microelectromechanical system) and its cavity width may be electronically controlled (thereby making it possible to choose the wavelength that passes through the cavity).

In another example, the measurement detector 5 and/or the reference detector 6 is a CCD (charge coupled device) matrix or a CMOS (complementary metal oxide semiconductor) matrix associated with one or more linear-variable or discrete optical filters.

The filter then allows measurements to be carried out at many wavelengths in the wavelength range considered (from 800 to 1250 nm).

In another embodiment, as illustrated in FIGS. 7 and 8, the measurement detector 5 is located on the same side as the waveguide 3 and fastened to said waveguide by means of a fourth volume 34 attached to the second volume 32 in the positive-X direction. The fourth volume 34 is a volume for holding the measurement detector 5. It is pressed against, preferably bonded to, on a first face 341, the second window 43 of the measurement cell 4.

The measurement detector 5 is for its part pressed against, preferably bonded to, a second face 342, opposite the first face 341, of the fourth volume 34.

The measurement cell 4 is still shown in the form of a segment of a tube of rectangular cross section. It comprises in this embodiment, on the wall 41, the two rectangular coplanar windows 42, 43 of substantially identical size.

On the opposite sidewall 44 a region for reflecting the light, comprising two reflective facets 45, 46, oriented at 90° to each other, allows a light beam entering via the first window 42 (in the direction oriented along the positive-Y direction), to be reflected towards the second window 43 (in the direction oriented along the negative-Y direction). The two reflective facets 45, 46 are in the present example formed of planar surfaces, oriented for the first at 45° in the XY plane and for the second at 135° in the same plane.

They are separated by a facet 47, mainly planar and parallel to the X-axis.

The two reflective facets 45, 46 are dimensioned so as to return the entire measurement beam 22 emerging from the first window 42 towards the second window 43.

Their reflective character is, in the present embodiment, obtained by polishing and local metallization of the surface (for example with chromium) forming the lateral face of the measurement cell 4, this metallization being carried out by means known to a person skilled in the art. These facets may also be obtained by bonding mirrors onto the faces oriented at 45° and 135°, or by another other suitable means.

In order to measure the absorption spectrum, the measurement beam 22, when output from the waveguide 3, as illustrated in FIG. 7, passes therefore through the first window 42, is reflected within the fluid analyzed in the measurement cell 4 by the two plates 45, 46 and exits from said measurement cell 4 by passing through the second window 43. The attenuated measurement beam 22 is finally sensed by the measurement detector 5 placed on the optical pathway of the measurement beam 22.

The reference beam 23, for its part, is sensed, when output from the third volume 33 of the waveguide 3, by the reference sensor 6.

The measurement detector 5 and the reference detector 6 are identical to those of the embodiment described above.

In a variant embodiment of the waveguide 3, to improve the collimation and the separation of the beam emitted by the light source 2, the spherical face 313 of the first volume 31 of the waveguide 3 is not metallized over the entire length L but has a region absorbent to the wavelengths of the light source 2. Said region of thickness e, symmetric relative to the Z-axis and centered on the Z-axis is neither polished nor metallized.

In an improved variant embodiment, as illustrated in FIGS. 9a and 9b, the first volume 31 is truncated, in the XZ plane at the second end 312 and symmetrically relative to the Z-axis, by a substantially V-shaped cutout. The first volume 31 is, in the YZ plane, substantially M-shaped (FIG. 9b). The two faces 313a, 313b opposite the light source are polished and metallized. It is noted that this V-shaped cutout does not have an optical function. It is used to optimize the volume and therefore the cost of producing the part.

In operation, when a control unit 17 associated with the spectrometer 10 has been initialized for a type of fluid to be analyzed (selection of the wavelengths to be observed), said control unit 17 turns on the light source 2 at regular intervals the spacing of which has been chosen beforehand.

After a suitable period of time, taking account of the normal initialization time of said light source 2, the control unit 17 controls, when the spectrometer 10 is equipped with variable filters, means for varying the value of the variable filter so as to set said filters in succession to the various wavelengths forming a series necessary for determining the composition of the fluid analyzed, these wavelengths being stored beforehand in a memory of said control unit 17.

For each wavelength selected, the measurement detector 5 delivers a measurement characterizing the light intensity received at this wavelength.

The spectrometer 10 thus delivers, at regular intervals, measurements of the absorption spectrum of the fluid to be analyzed to the control unit 17.

Simultaneously, the reference detector 6 delivers, for the same wavelengths, a characteristic measurement of the light intensity received at each wavelength.

The control unit 17 compares the measurement value and the reference value and deduces therefrom the absorption due to the sample contained in the measurement cell 4.

Based on an algorithm or a table of values stored in memory the control unit 17 determines, at regular intervals, modifications to operating parameters of the engine 16. For example: whether the fuel is suitable for the engine, setting of the ignition advance, setting of the injection, etc.

The treatment of the signal output from the spectrometer 10 according to the invention is beyond the scope of the present invention, and it is not described in greater detail here.

Among its various advantages, the spectrometer 10 as described is therefore a reliable system, using simple and robust components, capable of taking into account drift and aging, and that therefore may be used in a difficult environment such as the automobile environment.

The use of a waveguide 3 according to the invention advantageously allows the collimating lens and the beam splitter of a conventional spectrometer to be replaced, the mechanical tolerances of the waveguide 3 to be reduced, since there is now only a single part, and problems with condensation on the surface of the optical components to be obviated, without additional cost.

The measurement carried out is virtually continuous, thereby allowing the system to be matched to various tests (fuel, oil, urea, etc.) for which the required intervals between measurements are of different lengths.

The use of a reference optical pathway allows a significant drift in the light sources (for example light emitting diodes) to be taken into account. It is therefore possible to envision using the spectrometer 10 over a wide range of temperatures (typically in the range corresponding to the automotive field: −40° C. to +105° C.)

The spectrometer 10, by virtue of its reference optical pathway, also allows self-calibration (measurements carried out with the light turned off and with maximum light characterize the electronic noise of the detectors) without emptying the measurement cell, which is an absolute requirement for a simple measurement in an environment such as a fuel tank or a pipe of an automotive vehicle. This self-calibration may moreover be carried out at intervals as closely spaced as required, so as to take into account the aging of the components of the spectrometer.

It is also noted that the concept described is particularly economical for industrial scale mass production, in the case where the measurement is made at more than five wavelengths, this being the case for measurement of fuel parameters or for a multiuse instrument suitable for various fluids to be analyzed, and therefore having to accommodate absorption measurements at several tens of wavelengths.

In the contrary case, for example for a spectrometer requiring measurements at five preset wavelengths, a configuration comprising five light emitting diodes of different wavelengths, each exactly matching a measurement wavelength, and used together as a light source 2, offers a less expensive device (because the wavelength filter associated with each detector is no longer required).

Among the applications which may be considered for the spectrometer described above, it is naturally possible to mention a vehicle-borne sensor of fuel, oil, coolant or urea quality.

The scope of the present invention is not limited to the details of the embodiments considered above by way of example, rather it includes modifications within the capabilities of a person skilled in the art.

As a variant, the measurement cell 4 has a cylindrical cross section. In this variant, the measurement principle remains unchanged, as long as the geometry of the measurement cell 4 is precisely known. More generally, any measurement cell 4 geometry is acceptable, provided that it is possible to calibrate the spectrometer 10.

Clearly the light source 2 may be formed of a single, wide-emission-spectrum light emitting diode, or in contrast of a larger number of diodes, if the emission characteristics of the light emitting diodes and the desired emission spectrum require it. These light emitting diodes, the combined power of which does not exceed a few tenths of a watt, are supplied with power by known means, details of which are not given here.

The exemplary embodiment is described for a light source 2 comprising light emitting diodes. Clearly other diodes, alone or in combination, can be used, either, depending on the state of the art, low-unit-cost diodes with wider spectra or, with the aim of creating a spectrum in another wavelength range It is understood that the light emitting diodes chosen are commercially available products having a very low unit cost. An equivalent light source 2 has therefore been created based on available components that are very cheap, with the aim of minimizing the overall cost of the spectrometer 10. Moreover, light emitting diodes are known to have a lifetime (period of time before the power emitted has halved) of several tens of thousands of hours, therefore compatible with the lifetime required by an automotive-vehicle-borne instrument. However, the invention may still be used by any light source, for example an incandescent lamp, etc.

The description given concerned a transmission spectrometer, for which the spectrum measured is the spectrum of the light having passed through the fluid. The principle described is equally applicable to a reflection spectrometer, measuring the light reflected by a fluid, without essential modification of the device.

Other variant embodiments are also possible, as for example producing an integrated waveguide 3 and measurement cell 4 from the same material.

The invention claimed is:

1. A vehicle-borne spectrometer for measuring a spectrum of a light beam in a pre-determined wavelength range, the spectrum being generated by a fluid to be analyzed, said spectrometer comprising:
   at least one light source defining an orthogonal coordinate system;
   a waveguide configured to shape an incident optical beam emitted by the at least one light source, and divide said optical beam into a measurement beam and a reference beam;
   a measurement cell, comprising at least two walls comprising the fluid to be analyzed, wherein a flow direction of the fluid into the measurement cell defines a longitudinal axis Z, a transverse axis Y that is normal to said at least two walls, and an axis X that is orthogonal to both the axis Z and the axis Y;
   a measurement detector, placed on an optical pathway taken by the measurement optical beam, encountering the measurement cell; and
   a reference detector, placed on an optical pathway taken by the reference optical beam, not encountering the measurement cell,
   characterized in that the waveguide consists of a single unit, the single unit comprising:
   a first volume, which has a thickness (e) along the axis X, for forming and separating the incident beam emitted by the light source into two substantially parallel and identical beams, said light source being pressed against a first end of the first volume;
   a second volume having a thickness equal to that of the first volume for guiding the measurement beam towards the measurement detector, said second volume being pressed, via a free end, against a first wall of the measurement cell; and
   a third volume having a thickness equal to that of the first volume for guiding the reference beam towards the measurement detector, said third volume being pressed, via a free end, against the reference detector.

2. The spectrometer as claimed in claim 1, wherein the first volume comprises, at a second end, opposite a first end, an internal reflective face, treated at least on a part of its surface so as to reflect the incident beam emitted by the light source.

3. The spectrometer as claimed in claim 1, wherein the first volume comprises, substantially at the first end and on either side of the light source, a face treated so, as to direct the measurement beam and the reference beam, respectively, into the second volume and the third volume, respectively, of the waveguide.

4. The spectrometer according to claim 1, wherein the waveguide comprises a fourth volume for holding the measurement detector, said measurement detector being pressed, by said fourth volume, against the first wall of the measurement cell.

5. The spectrometer as claimed in claim 1, wherein untreated faces of the waveguide absorb or scatter wavelengths emitted by the light source.

6. The spectrometer as claimed in claim 1, wherein the waveguide is made of a plastics material that allows the spectrum emitted by the light source to pass.

7. The spectrometer as claimed in claim 1, wherein the waveguide is made of glass and allows the spectrum emitted by the light source to pass.

8. The spectrometer as claimed in claim 1, wherein the measurement detector and reference detector are each associated with a wavelength filter.

9. The spectrometer as claimed in claim 8, wherein the wavelength filters are variable filters and are configured to vary the value of said variable wavelength filters.

10. The spectrometer as claimed in claim 1, wherein the light source is formed by four light emitting diodes (LEDs) the emission spectrum of which covers a wavelength range corresponding to the fluid to be analyzed, said light emitting diodes being arranged in a square and as close to one another as possible.

11. The spectrometer as claimed in claim 1, wherein the light source is an incandescent lamp.

12. The spectrometer as claimed in claim 1, wherein the waveguide and the measurement cell are integrated.

13. A sensor of fuel, oil, coolant or urea quality intended to be installed permanently in a vehicle, characterized in that said sensor comprises a spectrometer as claimed in claim 1.

14. A method for controlling at least one operating parameter of a vehicle engine, said vehicle being provided with a sensor as claimed in claim 13 equipped with variable wavelength filters, and an electronic control unit connected to said sensor, said method comprising:

selecting a fluid to be analyzed;

turning on a light source at regular intervals;

waiting for a suitable period of time, taking account of the normal initialization time of said light source;

controlling the variable wavelength filters so as to set said filters in succession to the various wavelengths forming a series necessary for determining a composition of the fluid analyzed, the wavelengths being stored beforehand in a memory of said control unit for each fluid likely to be analyzed by the sensor;

measuring, for each wavelength selected, using the measurement detector and the reference detector, the light intensity received at the wavelength;

transmitting to the control unit, at regular intervals, measurements of the absorption spectrum of the fluid to be analyzed and measurements of the reference spectrum;

comparing, using the control unit, the measurement value and the reference value;

determining, using the control unit, the absorption due to the sample contained in the measurement cell; and determining, based on an algorithm or a data table stored in memory, using the control unit, at regular intervals, modifications to the operating parameters of the engine.

15. The sensor, as claimed in claim 13, further comprising a vehicle attached thereto.

\* \* \* \* \*